United States Patent [19]

Kesling

[11] Patent Number: 5,013,239
[45] Date of Patent: May 7, 1991

[54] POSITIONER WITH ROTATIONAL CONTROL ELEMENTS

[75] Inventor: Christopher K. Kesling, LaPorte, Ind.
[73] Assignee: TP Orthodontics Inc., Westville, Ind.
[21] Appl. No.: 411,667
[22] Filed: Sep. 25, 1989
[51] Int. Cl.$^5$ ............................................... A61C 7/00
[52] U.S. Cl. ...................................................... 433/6
[58] Field of Search ............................. 433/6; 128/861

[56] References Cited

U.S. PATENT DOCUMENTS

| | | | |
|---|---|---|---|
| 3,510,946 | 5/1970 | Kesling | 433/6 |
| 3,837,081 | 9/1974 | Kesling | 433/6 |
| 4,591,341 | 5/1986 | Andrews | 433/6 |
| 4,793,803 | 12/1988 | Martz | 433/6 |

*Primary Examiner*—Gene Mancene
*Assistant Examiner*—Michael Lynch

[57] ABSTRACT

A tooth positioner having rotational control elements for providing better rotational control to the teeth engaged by the elements wherein the elements are in the form of U-shaped members fitting over adjacent edges of teeth and where the U-shaped elements may be interconnected by a strand of non-stretchable material.

12 Claims, 2 Drawing Sheets

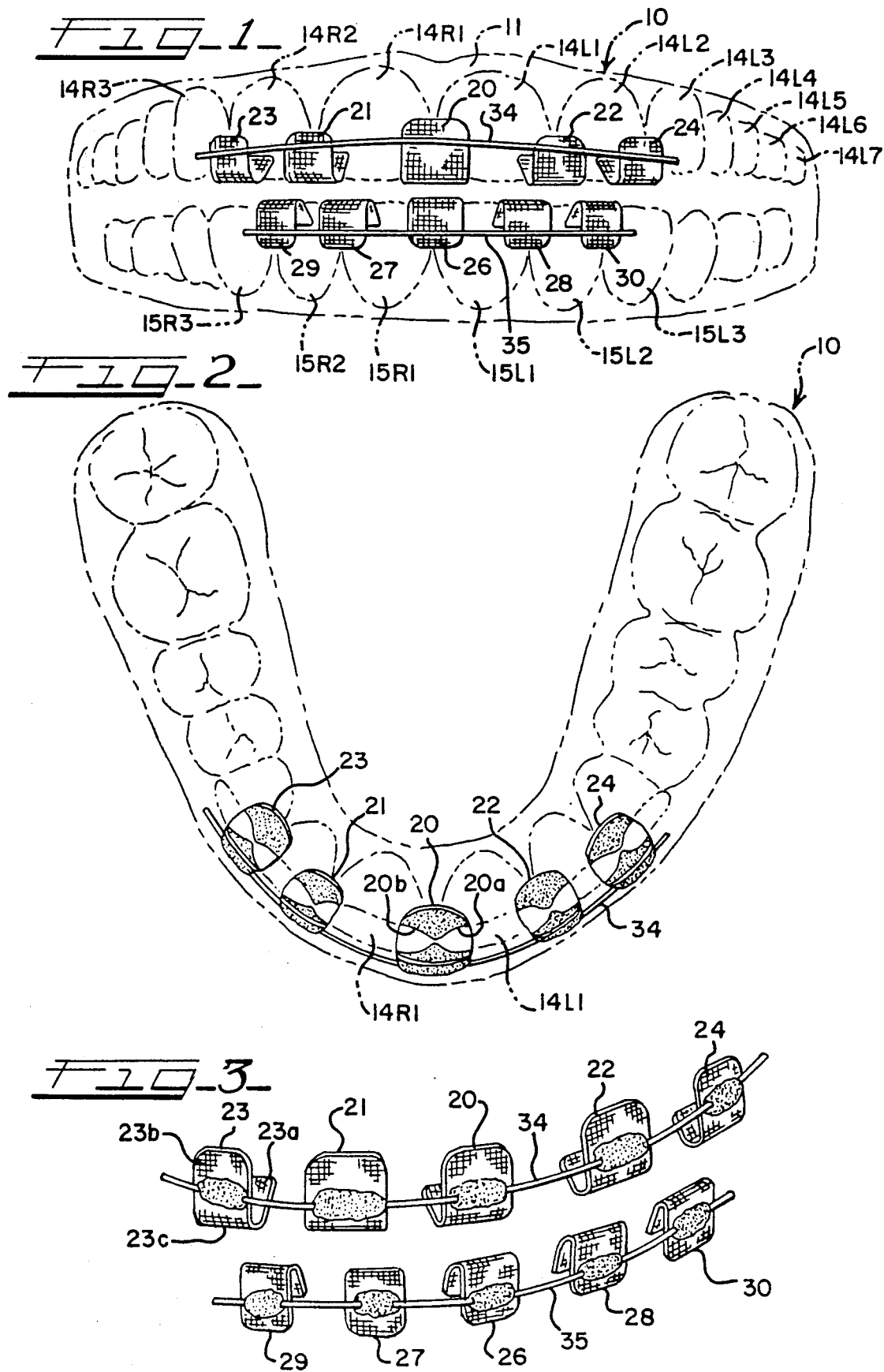

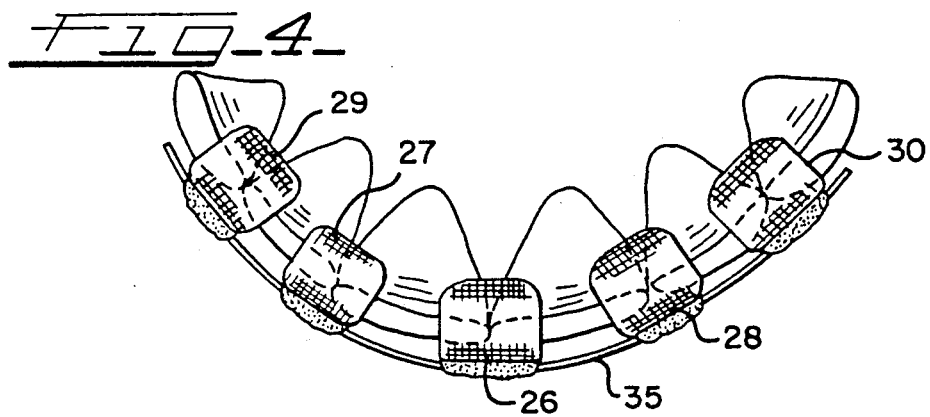
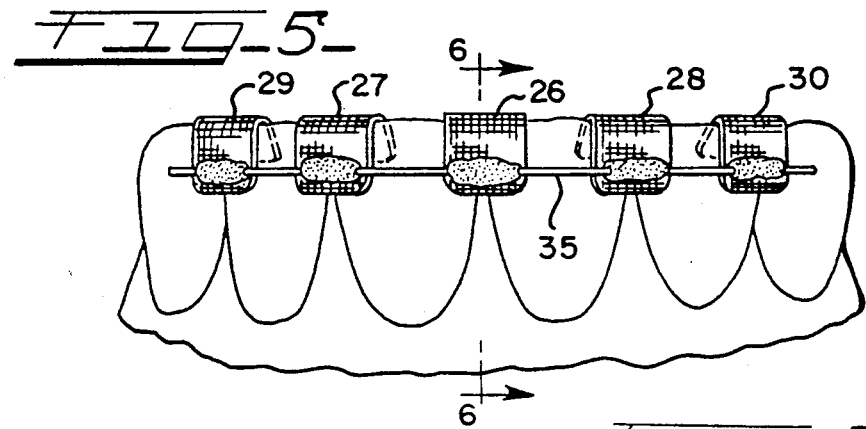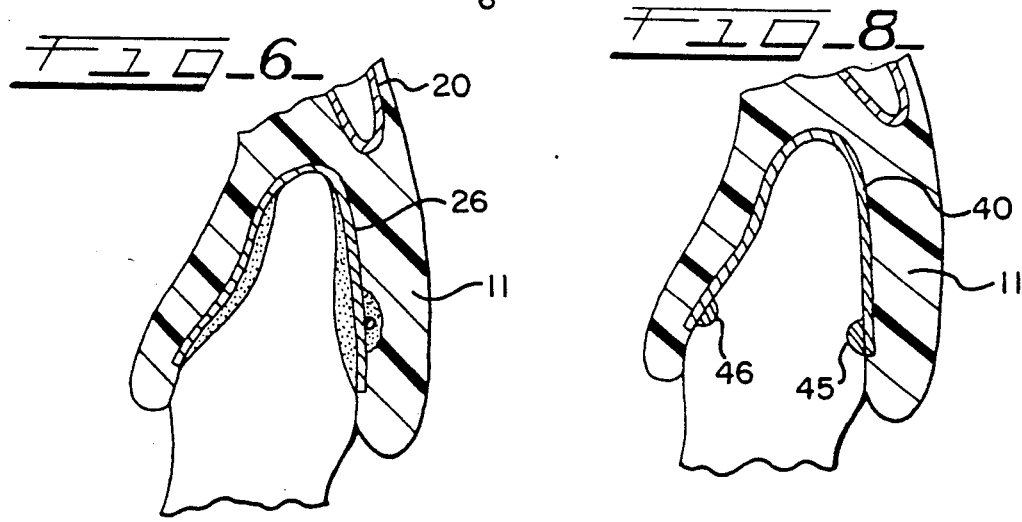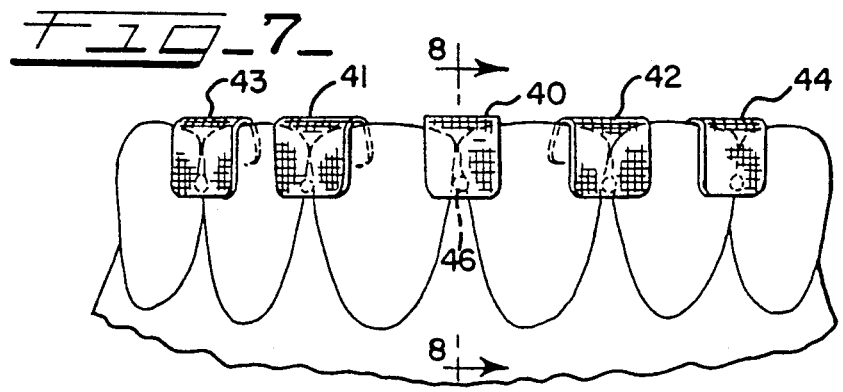

POSITIONER WITH ROTATIONAL CONTROL ELEMENTS

This invention relates in general to an orthodontic appliance, and more particularly to a tooth-positioning appliance, and still more particularly to a tooth-positioning appliance having one or more rotational control elements functioning to engage adjacent edge portions of teeth where the elements are molded into the positioner.

BACKGROUND OF THE INVENTION

Heretofore, it has been well known to provide an orthodontic appliance in the form of a tooth positioner having a molded arch-shaped body of resilient material with sockets for engagement with the teeth of one or both arches of a person. It has also been well known to mold rigid means into the body of the positioner for enhancing positioning and orientation of the appliance and in some respects to control rotation as shown in U.S. Pat. No. 3,510,946. The rigid elements shown in this patent are designed to fit directly over one or more selected teeth, and more particularly to fit over a portion or all of a tooth. However, the elements are independent of one another and rely strictly upon the relationship between the appliance body and the element to which it is formed.

SUMMARY OF THE INVENTION

The orthodontic appliance of the present invention is in the form of an elastomer tooth-positioning appliance that may be custom-made or preformed, and which includes at least one anti-rotation element molded in the body of the appliance of substantially more rigid material than the appliance body, and which overcomes the difficulties heretofore experienced in that more positive rotational control is obtained. The elements used for increasing rotational control are formed of a material substantially more rigid than the body of the positioner and to engage edge portions of adjacent teeth so that a better relationship between adjacent teeth can be obtained. The elements may be made of acrylic or metal and when used in plural are preferably interconnected with a strand of non-stretchable material such as a titanium wire so as to maintain the positive interrelationship between adjacent elements.

It is therefore an object of the present invention to provide a new and improved positioner with rotational control elements to increase rotational control of teeth.

Another object of the invention is in the provision of a new and improved positioner having rotational control elements that coact to function concurrently on edge portions of adjacent teeth to not only control rotation but to better improve and/or maintain the proper relationship between adjacent teeth.

A still further object of the invention is in the provision of a new and improved tooth-positioning appliance having a plurality of interconnected rotational control elements molded in the body of the appliance and of a material that is substantially more rigid than the appliance body and which function to engage adjacent edge portions of teeth.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a front elevational view of a tooth-positioning appliance according to the invention and illustrating for purposes of clarity the body of the appliance in phantom to show the rotational control elements of the present invention and their relationship with the teeth of the maxillary and mandibular arches as the elements are associated with sockets in the appliance;

FIG. 2 is a top plan view of the appliance of FIG. 1 again showing the appliance body in dotted lines and the rotational control elements in solid lines and particularly illustrating the manner in which the elements relate to adjacent sockets of the appliance;

FIG. 3 is a perspective view of the rotational control elements prior to being molded into the body of the appliance to illustrate their general structure;

FIG. 4 is a top plan view of the rotational control elements interconnected together and prior to being molded into the body of the appliance for purposes of illustrating the manner in which the elements engage the teeth;

FIG. 5 is a front elevational view of the arrangement shown in FIG. 4;

FIG. 6 is a transverse sectional view taken through one of the control elements and particularly along lines 6—6 of FIG. 5 and also illustrating the body of the appliance as it relates to the control element;

FIG. 7 is a view similar to FIG. 5 but illustrating a further embodiment of the invention where the control elements are not connected together and where they include protuberances for fitting in the embrasures of the teeth; and FIG. 8 is an enlarged vertical sectional view taken along line 8—8 of FIG. 7 to further illustrate the manner in which the protuberances will fit between adjacent teeth.

DESCRIPTION OF THE INVENTION

The tooth-positioning appliance of the present invention provides improved rotational control by integrating one or more control elements of substantially more rigidity than the body of the positioner, wherein the element serves to bridge the contact area or space between adjacent teeth. The first tooth-positioning appliance ever made depended solely upon the resilient material of the body of the appliance to control rotation. Thereafter, socket liners for one or more teeth were molded into the resilient body of the positioner directly into and in alignment with sockets. The rigid elements in the positioner of the invention are provided in adjacent portions of adjacent sockets so as to simultaneously engage adjacent portions of adjacent teeth. Thus, the rotational control elements in the positioner of the present invention overlap edge portions of adjacent teeth so that support between those adjacent teeth is utilized to further enhance rotational control. Where a plurality of the rigid rotational control elements is provided, particularly for anterior teeth, they may be interconnected together by a flexible strand of wire so as to more positively maintain the relationship between adjacent rotational control elements that will in turn more positively control adjacent teeth particularly in the anterior of the mouth.

Referring now to the drawings, and particularly to FIGS. 1 and 2, a tooth-positioning appliance of the invention, generally indicated by the numeral 10, includes an arch-shaped body 11 of resilient material having a plurality of upper and lower sockets for upper and lower teeth of a patient. The upper sockets are identified by the numeral 14 and the lower by the numeral 15. Additionally, the upper sockets on the left side include the letter "L", while on the right side the letter "R". Finally, the sockets are numbered from the front from 1 to 7 beginning at the socket for the front central.

The tooth-positioning appliance 10 will usually be custom made from a setup such as disclosed in U.S. Pat. No. 2,531,222. The appliance is molded of a suitable resilient material such as rubber or a plastic and includes impressions or sockets of the teeth to urge teeth into preselected positions. However, the appliance may be preformed, although the control in a preformed appliance would not normally be as precise as that of a custom-made appliance.

A tooth-positioning appliance is normally made for engaging teeth of both the maxillary and mandibular arches, but it will be appreciated that it may be made for engaging only some or all of the teeth in one of the arches. It is primarily useful to speed up the removal of fixed appliances and serve as the final treating device to complete movement of the teeth into their most ideal occlusion positions and then to thereafter retain those positions.

Where a tooth has initially been rotated a considerable amount to a corrected position, the rotational control elements for a positioner become important to control rotation, as rotated teeth would normally have a tendency to move back to their original position until they are properly set. A positioner, most generally prescribed immediately upon removal of fixed appliances, is effective to finalize movement then because the teeth are still mobile. The rotational control elements or inserts molded in the resilient body of the appliance are usually applicable for the anterior teeth to control rotation of the centrals, laterals and cuspids. However, the control elements may be used for other teeth as well. For aesthetics, proper masticating and overall health, it is important that anterior teeth be in the most desirable and effective positions.

As seen particularly in FIGS. 1 to 3, the rotational control elements include a central element 20 for the upper arch, adjacent but spaced elements 21 and 22, and further adjacent but spaced elements 23 and 24. Similarly, for the lower arch a central element 26 is flanked on opposite sides by elements 27, 28, 29 and 30. It will be appreciated that while rotational control elements are shown both for the upper and lower arches in this embodiment, they may be for either or both depending upon the desires of the orthodontist treating a particular patient.

The upper and lower central rotational control elements 20 and 26 are positioned to respectively span the adjacent edge portions of the upper and lower centrals, while the upper and lower elements 21 and 27 are positioned to respectively span the upper right central and lateral and the lower right central and lateral. With respect to the positioner appliance, the elements span the particular sockets that are to be engaged by the teeth. The upper and lower control elements 23 and 29 are positioned to respectively span the adjacent edge portions of the upper right lateral and cuspid teeth and the lower right lateral and cuspid teeth. Likewise, the upper and lower control elements 22 and 28 arranged on the left side of the appliance are positioned to respectively overlap the edge portions of the upper left central and lateral teeth and the lower central and lateral teeth.

Finally, the upper and lower rotational control elements 24 and 30 arranged on the left side of the appliance are positioned to respectively span or overlap the upper and lower left lateral and cuspid teeth.

In order to improve and maintain a proper interrelationship between the upper rotational control elements, they are interconnected by a nickel titanium wire or strand 34, while the lower elements are interconnected by a nickel titanium wire or strand 35. The interconnecting strand may be made of other materials as long as it is non-stretchable and flexible to allow some axial movement between elements.

While the elements must be of a material that is substantially more rigid than the material in the appliance body, the elements may be made of metal, plastic or ceramic. Where it is desired to conform the elements to the contour of the tooth surfaces, they may be easily made of a hard acrylic plastic. Prior to the molding of the positioner, the placement of the elements on the teeth forming the mold may be accomplished as individual placements and thereafter interconnected by the wire strand to hold them in proper place during the molding process and interconnect them in the appliance. Where the elements are made of acrylic plastic, additional acrylic plastic may be applied over the wire strand and attached to the elements to interconnect the wire strand to the elements. Where the elements are made of metal, the strand may be suitably soldered to the elements, or otherwise connected.

As seen in FIG. 3, each of the elements is U-shaped so that they include, as indicated by the element 23, a leg 23a that contacts or mates with the lingual surface of adjacent teeth, a leg 23b that contacts or mates with the labial or buccal surfaces of the teeth, and a bight portion 23c that may contact or mate with the incisal or occlusal edge of the teeth. Further, as seen in FIG. 2, the contacting surfaces of the element are contoured to complementarily fit the teeth and tooth sockets of the positioner. For example, element 20 includes a tooth-engaging surface 20a that matingly engages an edge portion of the upper left central and is contiguous with the walls of socket 14L1. Similarly, tooth-engaging surfaces 20b of element 20 mate with the upper right central and are contiguous with the walls of the upper right tooth socket 14R1 of the appliance. The elements engage both the labial and lingual surfaces of a respective tooth. It will be appreciated that the internal surfaces of the other rotational control elements are likewise formed to be contiguous with the respective sockets and will engage matingly with the respective teeth.

Where it may be desired to additionally incorporate a retention action between the rotational control elements and the teeth, protuberances may be added to the engaging surfaces of the elements, as illustrated in the embodiment of FIGS. 7 and 8. In FIG. 7, a plurality of rotational control elements 40 through 44 are shown in position on anterior teeth representing a mold for an appliance. As particularly seen in FIG. 8, a rotational control element 40 includes protuberances 45 and 46 in the form of round buttons which are capable of engaging in the interproximal areas between adjacent teeth below their points of contact. Inasmuch as a rotational control element of this type would need to have a spring function so as to be flexible enough to spread apart and come back together during the seating of the element, it is preferable that the element be made of a springy metal. Other springy materials may be used. Once these elements are seated so that they properly engage the surfaces of the teeth for which they are fitted, the protuberances or buttons 45 and 46 will snap into the interproximal areas between the teeth gingival to the contact areas both at the labial and lingual and then serve to additionally retain in place the entire appliance within which the elements are molded. Thus, it would be optional to provide a retention lug or button for the rotational control elements. Further, it should be appreciated that in this embodiment it is optional as to whether a strand of non-stretchable material be attached to the elements to interconnect them with each other.

In view of the foregoing, it will be appreciated that the present invention achieves materially improved rotational control through the use of substantially rigid control elements molded in the resilient positioner body to matingly span adjacent portions of teeth. The optional interconnecting wire further serves to improve and/or maintain the proper positions of the rotational control elements and also to exert a force on these elements in accordance with the rest position of the interconnecting wire.

It will be understood that modifications and variations may be effected without departing from the scope of the novel concepts of the present invention, but it is understood that this application is to be limited only by the scope of the appended claims.

I claim:

1. An orthodontic appliance comprising a molded arch-shaped body of resilient material, said body being formed to fit within the mouth of a person between the upper and lower arches and including a series of adjacent sockets for teeth of the arches arranged to urge at least some teeth into preselected positions, said sockets having a bottom wall to engage the incisal/occlusal surface of a tooth and opposed labial and lingual walls adapted to engage the respective labial and lingual surfaces of a tooth, and means substantially more rigid than said resilient material molded in the appliance body, said means positioned in said sockets so as to bridge two adjacent sockets and to concurrently overlap a portion of adjacent teeth at the labial and lingual surfaces to inhibit tooth rotation and enhance desired rotational corrections, said means conforming to the labial and lingual tooth surfaces.

2. An orthodontic appliance as defined in claim 1, wherein said means includes protuberances fitting between the adjacent teeth gingival to the contact areas.

3. An orthodontic appliance as defined in claim 2, wherein said means is flexible to snap in place.

4. An orthodontic appliance as defined in claim 2, wherein said rigid means is flexible to allow the protuberances to fit the teeth.

5. An orthodontic appliance as defined in claim 1, wherein a plurality of rigid means for plural combinations of adjacent teeth are molded in the appliance body, and wire means interconnecting said rigid means together.

6. An orthodontic appliance as defined in claim 1, wherein said rigid means is of metal.

7. An orthodontic appliance as defined in claim 1, wherein said rigid means is of a generally hard acrylic.

8. An orthodontic appliance as defined in claim 1, wherein said rigid means is U-shaped and formed to generally conform to the surfaces of the teeth.

9. An orthodontic appliance comprising a molded arch-shaped body of resilient material, said body being formed to fit within the mouth of a person between the upper and lower arches and including a series of adjacent sockets for teeth of the arches arranged to urge at least some teeth into preselected positions, said sockets contoured to substantially matingly receive the teeth, and at least one U-shaped member molded in the appliance body and positioned so that a portion of said U-shaped member is disposed in each of two adjacent sockets, said U-shaped member bridging said two sockets to overlap a portion of each of two adjacent teeth and overly at least a portion of the labial/buccal and lingual surfaces of the teeth to inhibit tooth rotation, said U-shaped member being non-resilient and substantially more rigid than the body.

10. An orthodontic appliance as defined in claim 9, wherein the appliance includes a plurality of U-shaped members for spaced sets of teeth, and a non-stretchable flexible wire molded in said body and interconnected to said U-shaped members.

11. An orthodontic appliance as defined in claim 10, wherein the U-shaped members are metal.

12. An orthodontic appliance as defined in claim 10, wherein the U-shaped members are rigid plastic.

* * * * *